(12) United States Patent
Ishii et al.

(10) Patent No.: US 11,393,596 B2
(45) Date of Patent: Jul. 19, 2022

(54) MEDICAL INFORMATION PROVIDING SYSTEM, SERVER, MEDICAL INFORMATION PROVIDING APPARATUS, MEDICAL INFORMATION PROVIDING MEDIUM, MEDICAL INFORMATION PROVIDING METHOD AND PROGRAM

(71) Applicants: National University Corporation Chiba University, Chiba (JP); Medipharm Co., Ltd, Tokyo (JP); Higashi-Nihon Medicom Co., Ltd., Gyoda (JP)

(72) Inventors: Itsuko Ishii, Chiba (JP); Iichiro Yokoyama, Chiba (JP); Masanori Ogawa, Tokyo (JP); Tadashi Nomoto, Gyoda (JP)

(73) Assignees: National University Corporation Chiba University, Chiba (JP); Medipharm Co., Ltd, Tokyo (JP); Higashi-Nihon Medicom Co., Ltd., Gyoda (JP)

( * ) Notice: Subject to any disclaimer, the term of this patent is extended or adjusted under 35 U.S.C. 154(b) by 606 days.

(21) Appl. No.: 16/080,718

(22) PCT Filed: Feb. 28, 2017

(86) PCT No.: PCT/JP2017/007853
§ 371 (c)(1),
(2) Date: Aug. 29, 2018

(87) PCT Pub. No.: WO2017/150547
PCT Pub. Date: Sep. 8, 2017

(65) Prior Publication Data
US 2019/0066825 A1 Feb. 28, 2019

(30) Foreign Application Priority Data
Mar. 1, 2016 (JP) .............................. JP2016-038643

(51) Int. Cl.
*G16H 70/20* (2018.01)
*G16H 70/40* (2018.01)
(Continued)

(52) U.S. Cl.
CPC ............. *G16H 70/20* (2018.01); *G16H 10/60* (2018.01); *G16H 15/00* (2018.01); *G16H 20/10* (2018.01); *G16H 70/40* (2018.01); *G16H 80/00* (2018.01)

(58) Field of Classification Search
USPC ........................................................ 705/2–3
See application file for complete search history.

(56) References Cited

U.S. PATENT DOCUMENTS

| 6,024,699 A * | 2/2000 | Surwit ................... G16H 20/10 128/920 |
| 2002/0095313 A1* | 7/2002 | Haq ........................ G16H 20/60 705/2 |

(Continued)

FOREIGN PATENT DOCUMENTS

| JP | H09-294802 A | 11/1997 |
| JP | 2002-197188 A | 12/2002 |

(Continued)

OTHER PUBLICATIONS

Nieuwlaat, et al., "Interventions for enhancing medication adherence", Cochrane Library, Cochrane Database of Systematic Reviews, 2014, Issue 11. (Year: 2014).*

(Continued)

*Primary Examiner* — Amber A Misiaszek
(74) *Attorney, Agent, or Firm* — Studebaker & Brackett PC

(57) ABSTRACT

A medical information providing system 1 includes a medication examination information extracting unit 21*d* and a database management unit 21*e* in a medication examination (Continued)

DB server 20. The medication examination information extracting unit 21*d* extracts information on clinical examination relating to a medication that requires clinical examination when it is prescribed from at least one of package insert data and prescription guideline data concerning functional decline of internal organs, for plural types of medications. In addition, the medication examination information extracting unit 21*d* generates a medication examination database in which the extracted clinical examination information on the medication and the medication are stored in association with each other. In response to a request from a terminal device 10, the database management unit 21*e* refers to the generated medication examination database and provides information related to the clinical examination of the target medication for the terminal device 10.

15 Claims, 9 Drawing Sheets

(51) Int. Cl.
*G16H 10/60* (2018.01)
*G16H 15/00* (2018.01)
*G16H 20/10* (2018.01)
*G16H 80/00* (2018.01)

(56) References Cited

U.S. PATENT DOCUMENTS

| | | | | |
|---|---|---|---|---|
| 2003/0078809 | A1* | 4/2003 | LaCour | G16H 40/67 705/3 |
| 2003/0144884 | A1 | 7/2003 | Mayaud | |
| 2003/0236683 | A1* | 12/2003 | Henderson | G16H 20/10 705/2 |
| 2007/0250346 | A1* | 10/2007 | Luciano, Jr. | A61J 7/0069 705/2 |
| 2011/0264696 | A1* | 10/2011 | Selaniko | A61J 7/0481 707/E17.014 |
| 2012/0166222 | A1 | 6/2012 | Howard et al. | |
| 2012/0296675 | A1* | 11/2012 | Silverman | G16H 50/50 705/3 |

FOREIGN PATENT DOCUMENTS

| | | |
|---|---|---|
| JP | 2012-133564 A | 12/2010 |
| JP | 2013-220184 A | 10/2013 |
| JP | 2014-016846 A | 1/2014 |

OTHER PUBLICATIONS

Bruce, Andrea, "Examining Diagnostic Bias Among Clinicians", Pacifica Graduate Institute, 2016, pp. 1-134. (Year: 2016).*
International Search Report and Written Opinion dated Mar. 28, 2017 in connection with PCT/JP2017/007853.
Partial Supplementary European Search Report dated Feb. 20, 2019 in connection with EP Patent Application No. 17760012.9.
Bisgin et al., Mining FDA drug labels using an unsupervised learning technique—topic modeling. BMC Bioinformatics. Oct. 18, 2011;12 Suppl 10:S11. doi: 10.1186/1471-2105-12-S10-S11. 8 pages.
Boyce et al., Using Natural Language Processing to Identify Pharmacokinetic Drug-Drug Interactions Described in Drug Package Inserts, Proceedings of the 2012 Workshop On Biomedical Natural Language Processing, Jan. 1, 2012, 206-13, XP55553326.
Chen et al., FDA-approved drug labeling for the study of drug-induced liver injury. Drug Discov Today. Aug. 2011;16(15-16):697-703. doi: 10.1016/j.drudis.2011.05.007. Epub May 20, 2011.
FDA: LTKB Benchmark Dataset, US Food & Drug Administration, XP55553750, Retrieved from the Internet: Aug. 2, 2019; URL: https://www.fda.gov/ScienceResearch/BioinformaticsTools/LiverToxicityKnowledgeBase/ucm226811.htm. 2 pages.
Ikoma et al., A study on filtering of the effect range with the package insert of the medicine, 2014 IEEE 38th International Computer Software and Applications Conference Workshops, Jul. 1, 2014;426-31, XP55553303, doi: 10 .1109/COMPSACW. 2014. 72 ISBN: 978-1-4799-3578-9.
Ikoma et al., A study on accuracy improvement of knowledge extraction from the medical package inserts, Artificial Intelligence Research, Apr. 9, 2015;4(2):38-44, XP55553293, ISSN: 1927-6974. doi:10.5430/air.v4n2p38.
NIH: Dailymed, US National Library of Medicine, Dec. 19, 2017; XP55553635, Retrieved from the Internet: Jul. 2, 2019; URL: https://dailymed.nlm.nih.gov/dailymed/. 3 pages.
Okuya et al., A proposal for a drug information database and text templates for generating package inserts. Drug Healthcare Patient Saf. Jul. 29, 2013;5:161-9. doi: 10.2147/DHPS.S43303. Print 2013.
Wood Su; "A protocol for drugs that require regular monitoring"; Prescriber; vol. May 4, 2014; Apr. 5, 2021; pp. 31-35; XP55842839; Retrieved from the Internet: https://wchh.onlinelibrary.wiley.com/doi/pdfdirect/10.1002/psb.1186 [Retrieved on Sep. 20, 2021] *Key Points; p. 33 *.

* cited by examiner

FIG. 3

PRESCRIPTION

P1 —
NAME OF PATIENT
AGE        SEX
ADDRESS
INSURANCE CATEGORY
:
:
:

P2 —
NAME OF MEDICAL INSTITUTION

CONTACT DETAILS

P3 —
FIXED TEST VALUES

| | |
|---|---|
| AST | CPK |
| ALT | WBC |
| ALP | HGB |
| T−BIL | PLT |
| CRE | SEG |
| eGFR | ST |
| Cys−C | TSH |
| K | HbA1C |

P4 —
MEDICATION-BASED TEST VALUES

<TABLET A, 17.5mg>    KIDNEY FUNCTION (EGFR, CRE, CYS-C) ← CHANGE
                        CA             8.5 − − L
                        ALB            3.5 − − −

<GRANULE B>             K              2.4 L L L
    :                         :
    :                         :
    :

FIG. 4

| DRUG CODE | DRUG NAME | TEST ITEM | PARAGRAPH NAME/ GUIDELINE NAME | CODE UNIT NAME | REFERENCE RANGE |
|---|---|---|---|---|---|
| xxxxxx | LIQUID C, FOR INJECTION | HYPERKALEMIA | CONTRAINDICATION | K | 3.5~4.8mEq/L |
| yyyyy | TABLET D, 50mg | PATIENT WITH NEPHROPATHY | CONTRAINDICATION | KIDNEY FUNCTION | |
| ... | ... | ... | ... | ... | ... |

MEDICAL INFORMATION PROVIDING SYSTEM, SERVER, MEDICAL INFORMATION PROVIDING APPARATUS, MEDICAL INFORMATION PROVIDING MEDIUM, MEDICAL INFORMATION PROVIDING METHOD AND PROGRAM

This Application is a National Stage filing under 35 U.S.C. 371 of International Patent Application Serial No. PCT/JP2017/007853, filed Feb. 28, 2017, which claims foreign priority benefits under 35 U.S.C. § 119(a)-(d) or 35 U.S.C. § 365(b) of Japanese Application Number 2016-038643, filed Mar. 1, 2016. The entire contents of these applications are incorporated herein by reference in their entirety.

TECHNICAL FIELD

The present invention relates to a medical information providing system, a server, a medical information providing apparatus, a medical information providing medium, and a medical information providing method and program.

BACKGROUND ART

Conventionally, a system for providing prescription information on medication for the purpose of proper use of medication is known.

For example, in the pharmaceutical proper use monitoring system described in Patent Document 1, important information (interactions, side effects, contraindications, etc.) necessary for safe use of medications is displayed on a list in different colors according to the extent (degree of importance) of prescription medications to be considered for proper use.

Patent Document 1: Japanese Patent Application Laid-Open No. 2002-197188

DISCLOSURE OF INVENTION

Problems to be Solved by the Invention

Some medications require a predetermined clinical examination at the time of prescription, and a doctor or pharmacist is required to ensure that a necessary clinical examination is performed when such medications are prescribed. Further, for a checking of prescription, the pharmacist is required to perform a high-quality checking of prescription after certainly grasping whether or not there are prescribed medications requiring a predetermined clinical examination when they are prescribed. However, the pharmaceutical proper use monitoring system described above does not determine which medications require a predetermined clinical examination when they are prescribed. Therefore, it is necessary for a doctor or pharmacist to sequentially check package inserts or the like as to whether or not they are medications that require a predetermined clinical examination when they are prescribed. However, it is not easy to sequentially check whether prescribed medications require a predetermined clinical examination when they are prescribed by a doctor or prepared by a pharmacist, because there are several tens of thousands of types of medications. For this reason, there are problems in terms of lowering the work efficiency of doctors or pharmacists, the certainty of the execution of the clinical examination or the quality assurance of checking of prescription or the like. As described above, according to the conventional art, it is not easy to check whether or not a prescribed medication requires clinical examination for a patient.

An object of the present invention is to make it easier to check whether or not a prescribed medication requires clinical examination for a patient.

Means for Solving the Problems

In order to achieve the object described above, a medical information providing system according to one aspect of the present invention including a terminal device and a server which are configured to be able to communicate each other, wherein the server comprising: a medication examination information extracting means for extracting information on clinical examination relating to a medication requiring clinical examination when it is prescribed from at least one of package insert data and document data showing prescription guidelines concerning deterioration of organ function, for a plurality of types of medications; a database generating means which generates a medication examination information database in which clinical examination information for the medication extracted by the medication examination information extracting means, is stored in association with the medication; and a medication examination information providing means for referring to the medication examination information database generated by the database generating means in response to requests from the terminal device to provide the information on clinical examination relating to the relevant medication for terminal device.

Effects of the Invention

According to the present invention, whether or not a prescribed medication requires clinical examination for a patient can be checked more easily.

BRIEF DESCRIPTION OF THE DRAWINGS

FIG. 3 is a schematic diagram showing an example of a prescription P (outside hospital prescription) output in the present embodiment.

FIG. 4 is a schematic diagram showing data contents of the medication examination information DB 22b.

PREFERRED MODE FOR CARRYING OUT THE INVENTION

Figure 1:
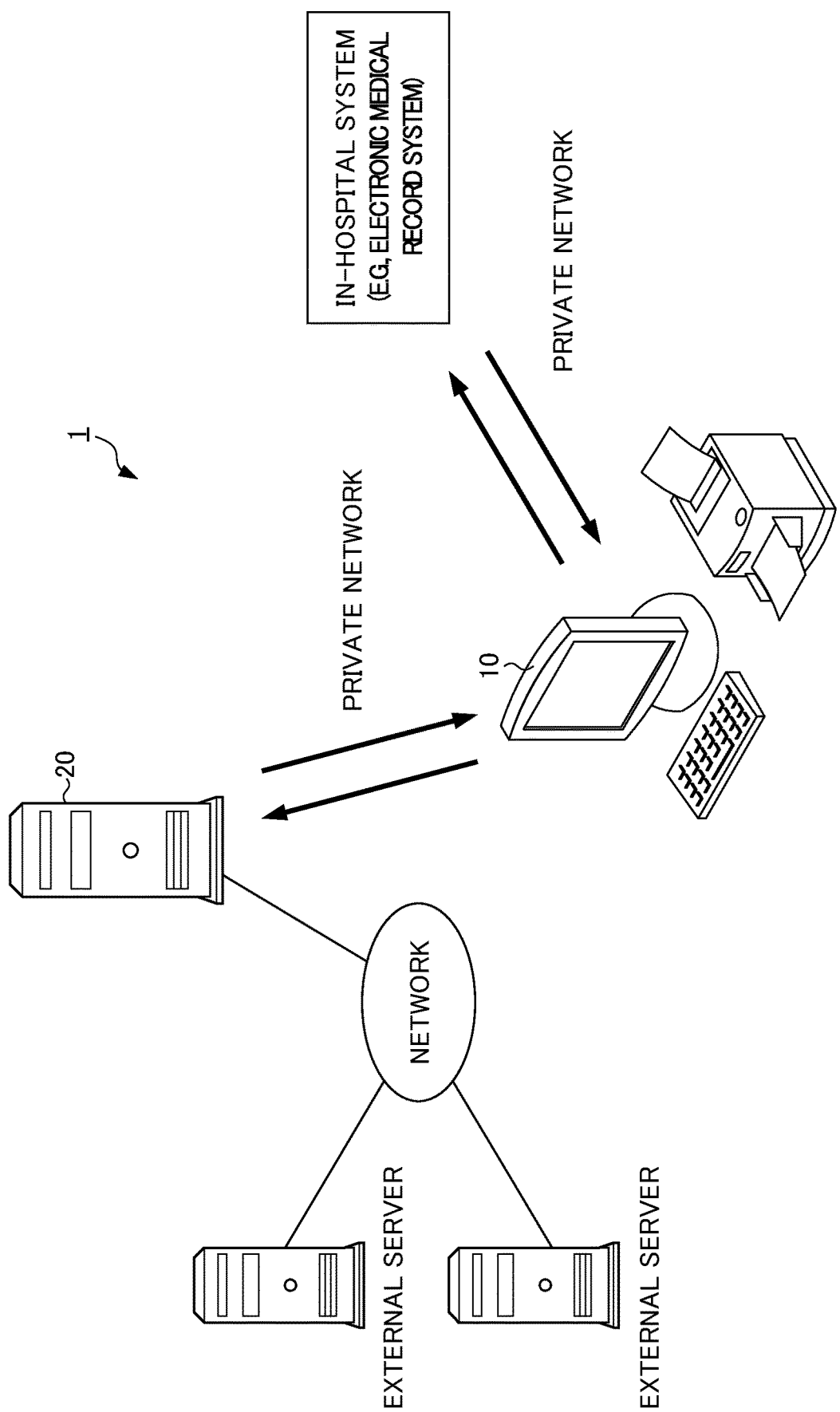
FIG. 1 is a diagram showing a system configuration of a medical information providing system 1 according to one embodiment of the present invention.

Embodiments of the present invention will be described below by referring to the drawings.

[System Configuration of Medical Information Providing System 1]

FIG. 1 is a diagram showing a system configuration of a medical information providing system 1 according to one embodiment of the present invention.

In this embodiment, the case where the medical information providing system 1 is configured as a prescription-issuing system to issue a prescription (here, an outside hospital prescription) will be described as an example.

As shown in FIG. 1, the medical information providing system 1 includes a terminal device 10 and a medication examination information database server (medication examination information DB server) 20. The terminal device 10 and the medication examination information DB server 20 are configured to communicate via a network such as a VPN (Virtual Private Network). In the present embodiment, the medication examination information DB server 20 can be configured as a cloud server. However, the medication examination information DB server 20 can also be configured as a dedicated physical server.

The terminal device 10 is configured by an information processing device such as a PC (personal computer). Further, the terminal device 10 is connected to various systems (hereinafter referred to as "in-hospital system") for managing information regarding patients, medical information of medications or the like, at a hospital, via a network such as a VPN.

The terminal device 10 is operated by a doctor or a person in charge of issuing prescriptions, and accepts an operation for issuing an outside hospital prescription for a patient whose medical care has been finished. When the operation for issuing the outside hospital prescription is performed, the terminal device 10 acquires the prescription data on the relevant patient, and a retrieval request as to whether or not the medications included in the prescription data require clinical examination is sent to the medication examination information DB server 20 (here, a medication whose amount must be adjusted due to reduced functions of organs is included). For a medication requiring clinical examination when it is prescribed, the laboratory data of the relevant patient is acquired from the in-hospital system, and the data is added to the prescription data. The terminal device 10 then issues an outside hospital prescription by, for example, printing the prescription data to which the test data has been added on a paper medium.

Forms for issuing outside hospital prescriptions may include not only printing them on a paper medium but also outputting as electronic data in a predetermined format or displaying them on a nonvolatile display (such as electronic paper). In addition, when an outside hospital prescription is output, it is possible to represent laboratory data items or laboratory data as one or two-dimensional barcodes as well as character strings. In this case, by reading the barcodes of the device such as a terminal on the patient or pharmacy side, the character strings of the laboratory data item or laboratory data can be displayed. Specifically, considering that it may not be appropriate for the patient or a third party to directly view the laboratory data items or laboratory data of the patient, part or all of the laboratory data items or laboratory data may be represented by barcodes.

The medication examination information DB server 20 refers, regarding various medications, to documentary data which include information on whether or not a medication requires clinical examination when it is prescribed, as well as the reference value or range of laboratory data, such as data of package inserts and guideline data related to prescriptions, and then automatically generates a medication examination information database (medication examination information DB) showing a list of medications requiring clinical examination when they are prescribed. For a medication which requires clinical examination when it is prescribed, reference values of laboratory data (threshold values) are set, and when there is one reference value of laboratory data, this reference value is taken as a boundary, and a range greater or smaller than this boundary (hereinafter referred to as "reference range") is suitable for prescribing the medication. On the other hand, if the reference value of laboratory data is set as the range (that is, upper limit and lower limit threshold values are set), the range between these thresholds is the reference range. The medication examination information DB server 20 stores this reference range for medications that require clinical examination when they are prescribed. When the medication examination information DB server 20 receives the retrieval request from the terminal device 10 as to whether or not the medications require clinical examination when it is prescribed, it retrieves the medication examination information DB. And the medication examination information DB server 20 transmits data of retrieved results including whether or not the retrieved medications require clinical examination when it is prescribed. If the medication requires clinical examination, the medication examination information DB server 20 transmits the data of retrieved results including the laboratory data items and reference ranges of laboratory data.

[Specific Configuration of Each Device]

Figure 2:
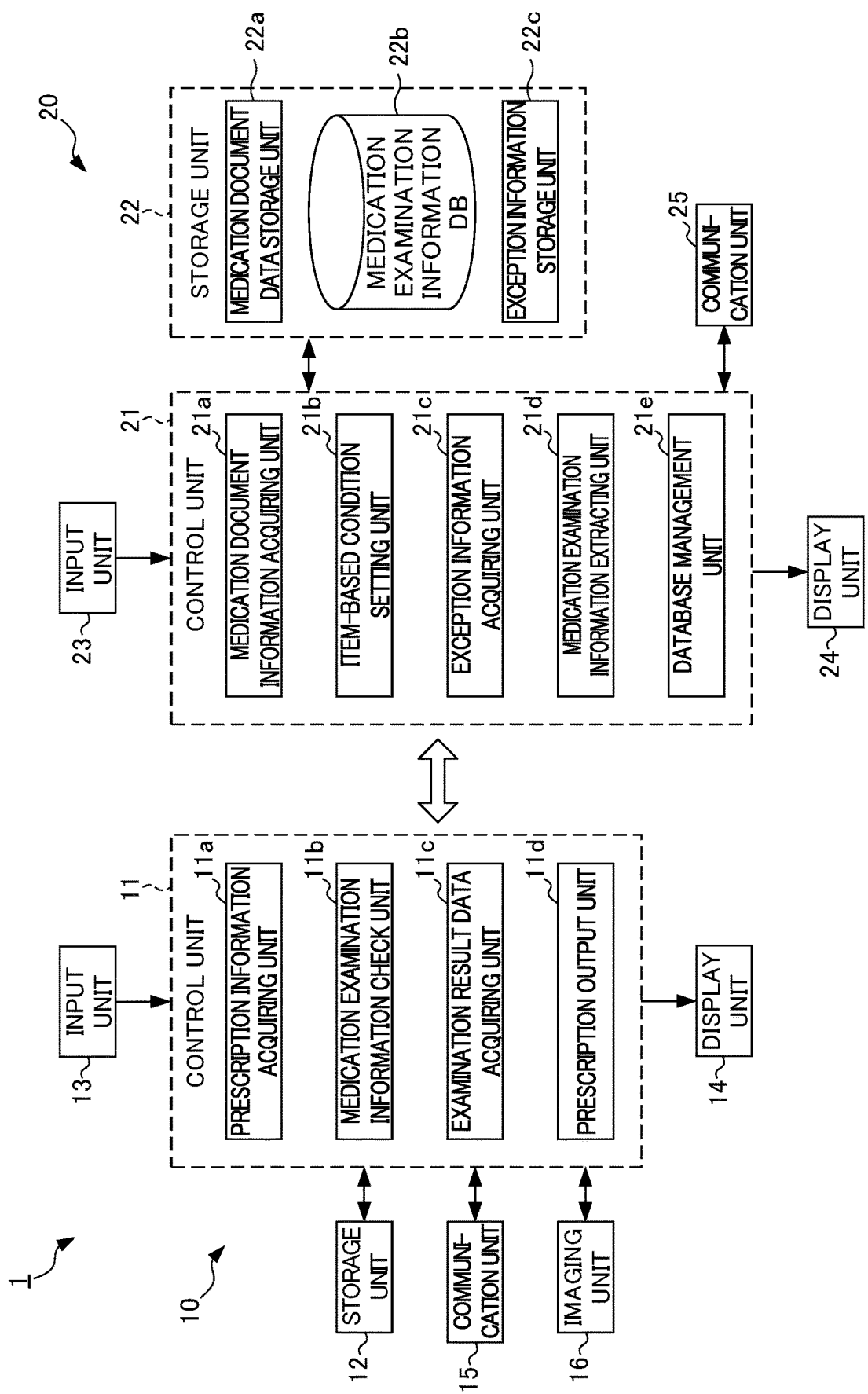
FIG. 2 is a block diagram showing the specific configuration of each device included in the medical information providing system 1.

Next, the specific configuration of each device in the medical information providing system 1 will be described. FIG. 2 is a block diagram showing the specific configuration of each device included in the medical information providing system 1.

[Specific Configuration of Terminal 10]

As shown in FIG. 2, in the medical information providing system 1, the terminal device 10 includes a control unit 11 that performs various arithmetic processing, a storage unit 12 that stores various types of information, an input unit 13 configured by such as a keyboard or a touch panel, a display unit 14 including a display, a communication unit 15 that controls communication performed with another device via a network, and an imaging unit 16 that captures an image, for a hardware configuration. For this type of terminal device 10, various programs are installed in the storage unit 12, and when the control unit 11 operates according to these programs, it performs functions including an outside hospital prescription issuing function.

In addition, for the terminal device 10 with this type of hardware configuration, a prescription information acquiring unit 11a, a medication examination information check unit 11b, an examination result data acquiring unit 11c, and a prescription issuing unit 11d are realized in the control unit 11 by running the program for prescription output processing described below.

The prescription information acquiring unit 11a acquires prescription data for a patient subject to issuance of a prescription, according to an operation to direct to issue a prescription via the input unit 13. At this time, the prescription information acquiring unit 11a acquires prescription data created by a doctor from an in-hospital system such as an electronic medical record system or accepts input of prescription data via the input unit 13, thereby acquiring the prescription data. The prescription information acquiring unit 11a, however, may acquire prescription data automatically by extracting the prescription medication data filed in an electronic medical record by the doctor.

The medication examination information check unit 11b checks whether or not each medication included in prescription data acquired by the prescription information acquiring unit 11a is stored in the medication examination information DB as a medication that requires clinical examination when it is prescribed. Specifically, the medication examination information check unit 11b sends a retrieval request for retrieving the medication examination DB to the medication examination information DB server 20 with the name of each medication in the prescription data as a key. The medication examination information check unit 11b then acquires the retrieval results sent by the medication examination information DB server 20.

The examination result data acquiring unit 11c refers to the retrieved result from the medication examination information DB server 20 acquired by the medication examination information check unit 11b, and if any medication which requires clinical examination when it is prescribed are included, laboratory data (hereinafter called "drug-specific laboratory data") regarding the patient corresponding to the relevant prescription are acquired from the in-hospital system. In the present embodiment, when acquiring the laboratory data from the in-hospital system, the examination result data acquiring unit 11c also acquires data for a predetermined number of times when the medication was prescribed to the patient in the past (in this case, three times). However, depending on the type of clinical examination, a valid period is set for each value of laboratory data, and the examination result data acquiring unit 11c acquires only data within the valid period from the in-hospital system.

When the prescription is issued, the examination result data acquiring unit 11c acquires the laboratory data regarding predetermined laboratory data items (hereinafter, referred to as "standardized laboratory data") common to all patients from the in-hospital system. Here, the standardized laboratory data are selected from those related to diseases causing serious side effects due to prescription of medications.

The prescription issuing unit 11d integrates the prescription data acquired by the prescription information acquiring unit 11a with the standardized laboratory data and drug-specific laboratory data acquired by the examination result data acquiring unit 11c, and for the patient concerned, outputs a prescription in which the prescribed medications are shown, as well as the laboratory data items and laboratory data of the relevant patient for prescribed medications those which require clinical examination when they are prescribed.

FIG. 3 is a schematic diagram showing an example of a prescription P (outside hospital prescription) output in the present embodiment.

As shown in FIG. 3, the prescription P output in the present embodiment includes a patient information area P1 showing information relating to a patient, a medical institution information area P2 showing the medical institution issuing the prescription P, a standardized laboratory data area P3 showing standardized laboratory data, and a drug-specific laboratory data area P4 showing drug-specific laboratory data.

In the patient information area P1, various types of information relating to the patient such as his/her name, age, sex, address, and insurance category, are shown.

In the medical institution information area P2, various information on the medical institution that have issued the prescription P, such as the name of the medical institution that have issued the prescription P, and contact information, is shown.

In the standardized laboratory data area P3, values relating to laboratory data items common to all patients are displayed as a list. As standardized laboratory data, all or part of laboratory data items, such as AST, ALT, ALP, T-BIL, CRE, eGFR, Cys-C, K, CPK, WBC, HGB, PLT, SEG, ST, TSH, and HbA1C, can be set. For these standardized laboratory data, it is effective to select values of laboratory data related to side effects that cannot be detected earlier through subjective symptoms as well as side effects where values of clinical laboratory data deviate before subjective symptoms appear.

In the drug-specific laboratory data area P4, laboratory data relating to medications requiring clinical examination when they are prescribed are displayed in a list. For example, in the drug-specific laboratory data area P4, the medication name "Tablet A, 17.5 mg" of a medication that requires a clinical examination when it is prescribed, a classification of laboratory data item (code unit name), laboratory data "renal function {eGFR, CRE, Cys-C}", "CA 8.5", "ALB 3.5", and the symbols "-", "L" or "H" indicating change of the value of laboratory data, are displayed in association with each other. Regarding the symbols showing change of the value of laboratory data, "-" means to be within the reference range, "L" means to be below the reference range, and "H" means to be above the reference range, respectively. In the prescription P in this embodiment, the change of value of laboratory data from left to right is shown in order of values of laboratory data for two times before, previous time, and current time (latest time). For example, when the change of the value of laboratory data is indicated as "- - L", the value of laboratory data was within the reference range two times before and the current time, while the latest value of laboratory data is lower than the reference range. In the drug-specific laboratory data area P4, if the value of laboratory data of a medication requiring a clinical examination when it is prescribed is not in the reference range, the laboratory data item may be shown in a particular way (by indicating with characters in red, underlining them, or the like).

By showing the change of past values of laboratory data on the prescription P in this way, it is possible to judge the state of the patient more accurately and to prescribe the medication more appropriately.

In the prescription P in this embodiment, as a classification for some laboratory data items, a code unit name representing a combination of a plurality of laboratory data items is shown. For example, a combination of three laboratory data items "eGFR", "CRE", and "Cys-C" are shown as a combination of laboratory data items for "renal function", because they are frequently cited for a number of medications. Here, the laboratory data of the laboratory data items in the combination are shown in other locations, for example as standardized laboratory data. However, if a combination of laboratory data items is shown, the laboratory data may be shown together. Further, instead of showing the laboratory data for the laboratory data items in the combination (or together with the laboratory data), the symbol "-", "L" or "H" indicating change of the value of laboratory data described above may be shown, and if the value of laboratory data is not within the reference range, the laboratory data item can be shown in a specific way (e.g., by indicating characters in red or underlining them).

By using the code unit name representing the combination of laboratory data items in this manner, it is possible to show laboratory data items requiring, for example, three lines as one line, and in the prescription area where the space available for description is not large, laboratory data can be shown effectively.

When the laboratory data items or laboratory data are represented by a barcode, one or both of the standardized laboratory data area P3 and the drug-specific laboratory data area P4 may be represented by a barcode, and specific laboratory data items or laboratory data in the standardized laboratory data area P3 and the drug-specific laboratory data area P4 may be represented by the barcode.

[Specific Configuration of Medication Examination Information DB Server 20]

As shown in FIG. 2, in the medical information providing system 1, the medication examination information DB server 20 includes a control unit 21 that performs various arithmetic processing, a storage unit 22 that stores various information, an input unit 23 implemented by a keyboard or the like, a display unit 24 including a display, and a communication unit 25 for controlling communication to be performed between other apparatuses via a network, for a hardware configuration. Such a medication examination information DB server 20 has various programs installed in the storage unit 22, and the control unit 21 operates according to these programs to perform a medication examination information DB generating function, a medication examination information DB update function, or a medication examination information DB retrieval function. In addition, the medication examination information DB server 20 with such a hardware configuration executes a medication examination information DB generating process or medication examination information DB update process described below, whereby a medication document information acquiring unit 21a, an item-based condition setting unit 21b, an exception information acquiring unit 21c, a medication examination information extracting unit 21d, and a database management unit 21e are realized in the control unit 21. Further, in the storage unit 22 of the medication examination information DB server 20, a medication document data storage unit 22a, a medication examination information DB 22b, and an exception information storage unit 22c, are stored.

The medication document data storage unit 22a stores package insert data relating to various medications acquired from an external database (including a database of pharmaceutical manufacturer and a public institution) for storing package insert data for various medications, as well as document data of guidelines acquired from an external database for storing document data of prescription guidelines relating to deterioration of organ (such as kidney) functions (ex.: Chronic Kidney Disease (CKD) clinical guidelines edited by the Japan Society of Nephrology). The documentary data stored in the medication document data storage unit 22a are updated in response to an update in the acquisition target database.

The medication examination information DB 22b stores laboratory data items necessary for prescription of medications and data of reference ranges of values of laboratory data in association with each other, for the various medications mentioned in the package insert and prescription guidelines concerning deterioration of organ function, and stores them.

FIG. 4 is a schematic diagram showing data contents of the medication examination information DB 22b.

As shown in FIG. 4, the medication examination information DB 22b stores a medication code which is a code unique to the medication, the name of the medication (product name or general name), a character string indicating laboratory data items extracted from package inserts or guidelines (laboratory data items), the paragraph name of the package insert or guideline name from which the character string has been extracted, the code unit name representing the laboratory data item category, and reference range data showing the reference range of laboratory data, in association with each other.

For example, on the first line of the medication examination information DB 22b in FIG. 4, for a medication with the code "xxxxxx" and medication name "liquid C for injection", the character string "hyperkalemia" is extracted from the paragraph "contraindicated", and the extracted result of "K" (potassium) as the code unit and "3.5-4.8 mEq/L" as the reference range of laboratory data are stored.

Each data of the medication examination information DB 22b is automatically generated by a medication examination information DB generating process described below. The content of the database may be confirmed by having the content of the automatically-generated medication examination information DB 22b approved by an expert such as a doctor or a pharmacist.

The exception information storage unit 22c stores exception information related to prescription of medications sequentially issued by a pharmaceutical manufacturer, a public institution or the like. For example, safety information (exceptional safety information) that is not described in package inserts or guidelines, such as emergency safety information issued by the Independent Administrative Institution of Pharmaceuticals and Medical Devices Agency, safety bulletin e-mail, etc., is stored in the exception information storage unit 22c as exception information.

When the exception information stored in the exception information storage unit 22c is to be included in any package insert or guideline due to updating or other reasons, the exception information stored in the exception information storage unit 22c is sequentially deleted by the exception information unit 21c.

The medication document information acquiring unit 21a acquires package insert data and document data of guidelines for various medications from an external database (a database of a pharmaceutical manufacturer, a public institution or the like) for storing package insert data for various medications, and an external database for storing document data of prescription guidelines relating to deterioration of organ function. In the present embodiment, the medication document information acquiring unit 21a accesses the external databases at a predetermined timing (for example, at every predetermined period such as once a month or when a specified direction is input), and acquires the package insert data and the document data of guidelines.

The item-based condition setting unit 21b sets extraction conditions for extracting character strings for laboratory data items, or reference value or range of laboratory data for various medications every item (usage, dose, contraindication etc.) of package inserts and guidelines in the package insert data and the document data of guidelines. For example, in the case of a package insert, extraction conditions are set for each item such as "usage/dose", "warning", "contraindication", and "pharmacokinetics". The extraction condition set here may be, for example, a word (character string) to be extracted, a predetermined word relevant to the word, or a character interval between these words (relation between the word to be extracted and a predetermined word). The extraction conditions set in this manner are stored in a predetermined storage area such as the storage unit 22 as a dictionary for each item. By setting the extraction conditions for each item of the package inserts and guidelines in the item-based condition setting unit 21b, it is possible to set more appropriate extraction conditions reflecting the descriptive features of each item. When the extraction condition includes a word (character string) to be extracted, a predetermined word relevant to the word, or a character interval between these words (a relationship between a word to be extracted and a predetermined word), it is possible to automatically and appropriately extract the laboratory data item, or the reference value or range of laboratory data, included in the package insert data and the document data of guidelines.

The exception information acquiring unit 21c sequentially acquires exception information (exceptional safety information) regarding prescription medications that is sequentially issued by the pharmaceutical manufacturer or public institutions, etc., and stores it in the exception information storage unit 22c. When the content of the exception information stored in the exception information storage unit 22c is to be included in a package insert or guideline due to update or other reasons, the exception information acquiring unit 21c sequentially deletes the exception information stored in the exception storage unit 22c.

In order to generate the medication examination information DB 22b, the medication examination information extracting unit 21d acquires the package insert data and the document data of guidelines of medications stored in the medication document storage unit 22a, and the item-based condition setting unit 21b extracts the character string of the laboratory data item and reference value or range of laboratory data for each medication in accordance with the set extraction conditions for each item. At this time, the medication examination information extracting unit 21d appropriately refers to the exception information stored in the exception information storage unit 22c, and if there is a character string of a laboratory data item or a reference value or range of laboratory data, which is not included in the data of the various documents stored in the medication document storage unit 22a, they are added to the character string extraction result. As a result, it is possible to retrieve laboratory data items and reference values or range of laboratory data, including safety information issued before updating the medication examination information DB 22b.

The medication examination information extracting unit 21d then converts the extracted laboratory data items to a code unit name representing the laboratory data item category based on the character strings of the laboratory data items and reference values or ranges of laboratory data for each medication. Further, the medication examination information extracting unit 21d stores the medication code which is a code unique to the medication, name (commercial name or general name) of the medication, a character string (laboratory data item) indicating the laboratory data item extracted in the package insert or guideline, the paragraph name of the package insert or guideline name from which the character string is extracted, the code unit name representing the laboratory data item category, and reference range data representing the reference range of laboratory data, in the medication examination information DB 22b, in association with each other.

When receiving a retrieval request from the terminal device 10, the database management unit 21e retrieves the medication examination DB 22b with the name of the medication specified in the retrieval request as a key, and transmits the retrieved result to the terminal device.

[Operation]

Next, the operation of the medical information providing system 1 will be described.

[Processing of Terminal Device 10]

Figure 5:
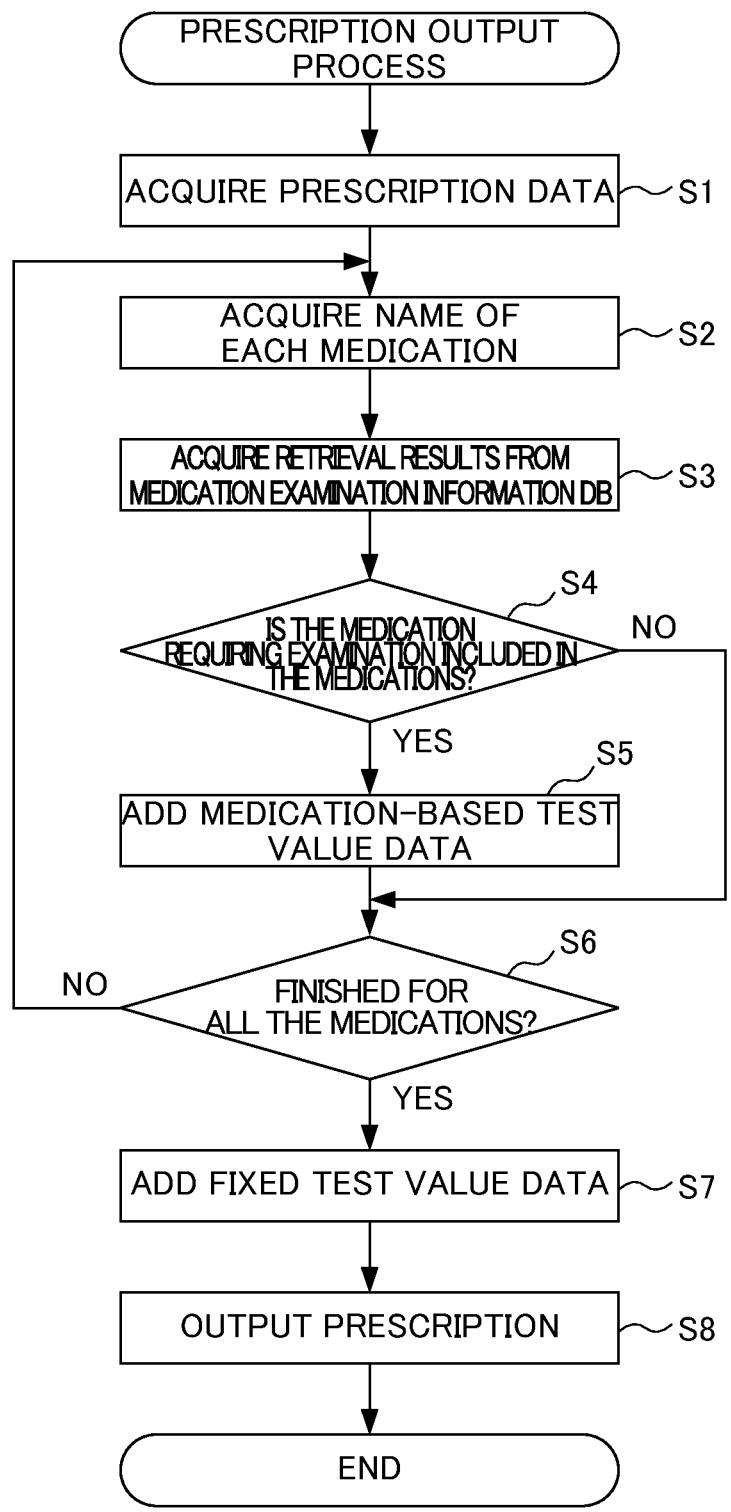
FIG. 5 is a flowchart showing the flow of prescription output processing executed by the terminal device 10.

FIG. 5 is a flowchart showing the flow of prescription output processing executed by the terminal device 10. The prescription output process is started in response to a directed input to execute the prescription output process via the input unit 13.

When the prescription output process is started, in step S1, the prescription information acquiring unit 11a acquires prescription data for a patient subject to issuance of a prescription.

In step S2, the medication examination information check unit 11b acquires the name of medications included in the prescription data.

In step S3, the medication examination information check unit 11b sends a retrieval request for retrieving the medication examination DB to the medication examination information DB server 20 with the name of each medication in the prescription data as a key, and acquires the retrieval results sent by the medication examination information DB server 20. When the medication examination information check unit 11b sends a retrieval request to the medication examination information DB server 20, in addition to using the name of the medication as a key, information that can uniquely identify the medication can be used as a key, so for example, the medication code can be used as a key.

In step S4, the examination result data acquiring unit 11c refers to the retrieved result from the medication examination information DB server 20 acquired by the medication examination information check unit 11b, and determines whether or not the medication requiring clinical examination is included in the medications for which a retrieval request has been made.

If the medication requiring clinical examination is included in the medications for which a retrieval request has been made, YES is determined in step S4, and the process proceeds to step S5.

On the other hand, if the medication that requires clinical examination is not included in the medications for which a retrieval request was made, NO is determined in step S4, and the process proceeds to step S6.

In step S5, the examination result data acquiring unit 11c acquires drug-specific laboratory data of a medication requiring clinical examination when they are prescribed for a patient corresponding to the relevant prescription from the in-hospital system, and adds them to the prescription data.

In step S6, the medication examination information check unit 11b determines whether or not retrieval of the medication examination information DB 22b has been finished for all the medications included in the prescription data.

When a retrieval of the medication examination information DB 22b has been finished for all the medications included in the prescription data, YES is determined in step S6, and the process proceeds to step S7.

On the other hand, if retrieval of the medication examination information DB 22b has not been finished for all the medications included in the prescription data, NO is determined in step S6, and the process proceeds to step S2.

In step S7, the examination result data acquiring unit 11c acquires standardized laboratory data from the in-hospital system for the relevant patient corresponding to the prescription, and adds the data to prescription data.

In step S8, the prescription issuing unit 11d integrates the prescription data acquired by the prescription information acquiring unit 11a with the data of standardized laboratory data and drug-specific laboratory data acquired by the examination result data acquiring unit 11c, and outputs the prescription (see FIG. 3).

After step S8, the prescription output process ends.

By such processing, if prescription data includes medications requiring clinical examination when they are prescribed, the laboratory data items and reference ranges of laboratory data are acquired from the medication examination information DB 22b, and value of laboratory data for the laboratory data items are acquired from the in-hospital system, so these data can be presented together with the patient's prescription.

In other words, according to the medical information providing system 1, it is possible to more easily check whether or not the prescribed medication requires clinical examination for the patient.

Therefore, according to the medical information providing system 1, it is possible to more certainly perform a necessary clinical examination of medications when they are prescribed.

In addition, the pharmacist auditing the prescription can clearly determine whether or not it is appropriate to prescribe the medication, because medications requiring clinical examination when they are prescribed are shown, and because the patient's values of laboratory data are shown on the prescription. This gives the pharmacist an opportunity to make doubt inquiries to the medical institution and make the grounds for doubt inquiries more reliable.

Therefore, according to the medical information providing system 1, it is possible to improve the quality of checking of prescription by a pharmacist (pharmaceutical management).

[Processing of Medication Examination Information DB Server 20]

Figure 6:
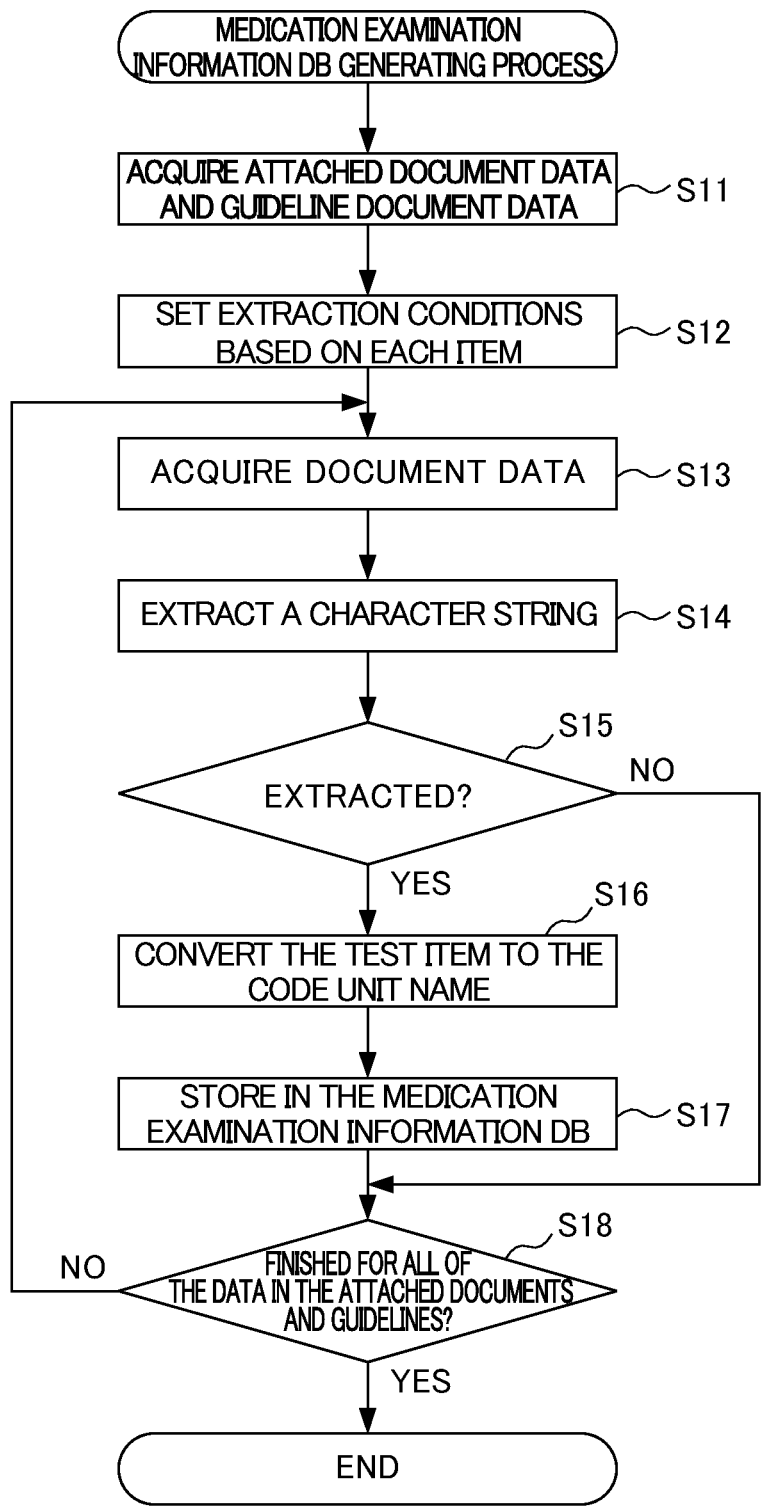
FIG. 6 is a flowchart showing the flow of the medication examination information DB generating process executed by the medication examination information DB server 20.

FIG. 6 is a flowchart showing the flow of the medication examination information DB generating process executed by the medication examination information DB server 20.

The medication examination information DB generating process is executed in response to an input for direction to execute the medication examination information DB generating process via the input unit 23, or a direction executed during a medication examination information DB update process described below.

When the medication examination information DB generating process is started, in step S11, the medication document information acquiring unit 21a acquires package insert data and document data of guidelines for various medications from an external database (a database of a pharmaceutical manufacturer, a public institution or the like) for storing package insert data for various medications, and an external database for storing document data of prescription guidelines relating to deterioration of organ function.

In step S12, the item-based condition setting unit 21b sets extraction conditions for extracting character strings for laboratory data items, or reference value or range of laboratory data for various medications every item (usage, dose, contraindication etc.) of package inserts and guidelines in data of package inserts and documents in guidelines. Here, as regards the extraction conditions for extracting the character string of the laboratory data item and reference value or range of laboratory data of each medication, it is also possible to store them as a preset setting file and to read this setting file.

In step S13, to generate the medication examination information DB 22b, the medication examination information extracting unit 21d acquires the package insert data and the document data of guidelines of medications stored in the medication document storage unit 22a.

In step S14, the medication examination information extracting unit 21d extracts the character string of the laboratory data item and a reference value or range of laboratory data, according to the item-based extraction conditions set by the item-based condition setting unit 21b.

At this time, the medication examination information extracting unit 21d appropriately refers to the exception information stored in the exception information storage unit 22c, and if there is a character string of a laboratory data item or a reference value or range of laboratory data, which is not included in the data of the various documents stored in the medication document storage unit 22a, they are added to the character string extraction result.

In step S15, the medication examination information extraction unit 21d determines whether or not character strings of laboratory data items and reference values or ranges of laboratory data for each medication have been extracted.

If the character strings of the laboratory data items and reference values or ranges of laboratory data for each medication have been extracted, YES is determined in step S15, and the process proceeds to step S16.

On the other hand, if the character strings of the laboratory data items and reference values or ranges of laboratory data for each medication have not been extracted, NO is determined in step S15, and the process proceeds to step S18.

In step S16, the medication examination information extraction unit 21d converts the extracted laboratory data items to a code unit name representing the laboratory data item category.

In step S17, the medication examination information extracting unit 21d stores the medication code which is a code unique to the medication, name (commercial name or general name) of the medication, a character string (laboratory data item) indicating the laboratory data item extracted in the package insert or guideline, the paragraph name of the package insert or guideline name from which the character string is extracted, the code unit name representing the laboratory data item category, and reference range data representing the reference range of laboratory data, in the medication examination information DB 22b, in association with each other.

In step S18, the medication examination information extracting unit 21d determines whether or not processing has been finished for all of the data in the package inserts and guidelines for each medication stored in the medication document data storage unit 22a.

If the process has not been finished for all of the package inserts and guidelines for each medication stored in the medication document data storage unit 22a, NO is determined in step S18, and the process proceeds to step S13.

On the other hand, if the process has been finished for all of the package inserts and guidelines for each medication stored in the medication document data storage unit 22a, YES is determined in step S18, and the medication examination information DB generating process ends.

Through such process, it is possible to extract medications requiring clinical examination when they are prescribed, from the package insert data and the document data of guidelines, and to automatically generate the medication examination information DB 22b including the laboratory data items and reference ranges of laboratory data. Therefore, compared with the case where the medication examination information DB 22b is generated manually, it is possible to reduce time and labor for generating the database, and it is possible to efficiently generate a database with more accurate contents.

Next, the medication examination DB update process executed by the medication examination information DB server 20 will be described.

Figure 7:
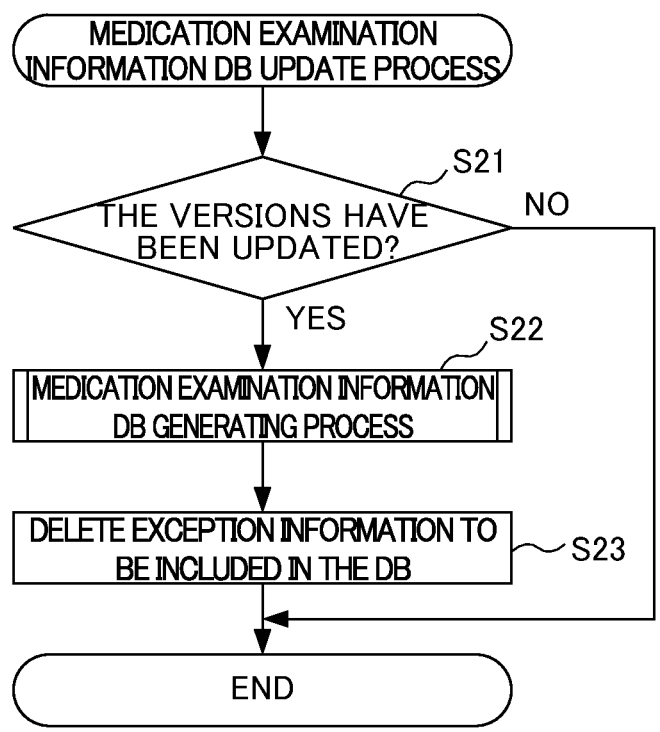
FIG. 7 is a flowchart showing the flow of the medication examination information DB update process executed by the medication examination information DB server 20.

FIG. 7 is a flowchart showing the flow of the medication examination information DB update process executed by the medication examination information DB server 20.

The medication examination information DB update process is started at a preset timing, such as every predetermined period.

When the medication examination information DB update process is started, in step S21, the medication document information acquiring unit 21a determines whether or not the versions of an external database (a database of a pharmaceutical manufacturer, a public institution or the like) for storing package insert data for various medications, and an external database for storing document data of prescription guidelines relating to deterioration of organ function, have been updated.

If there is a version update, YES is determined in step S21, and the process proceeds to step S22.

On the other hand, if the version has not been updated, NO is determined in step S22, and the medication examination DB update process ends.

In step S22, the medication document information acquiring unit 21a executes a medication examination information DB generating process.

In step S23, the exception information acquiring unit 21c deletes the exception information that is supposed to be included in the package inserts or guidelines due to update, or the like, from the exception information storage unit 22c.

After step S23, the medication examination information DB update process ends.

Through such processing, the contents of the medication examination information DB 22b are updated to the latest state, and a more appropriate prescription can be output.

[Modification 1]

In the embodiment described above, it is possible to implement the medical information providing system 1 as a system whose cloud is at a higher level.

Figure 8:
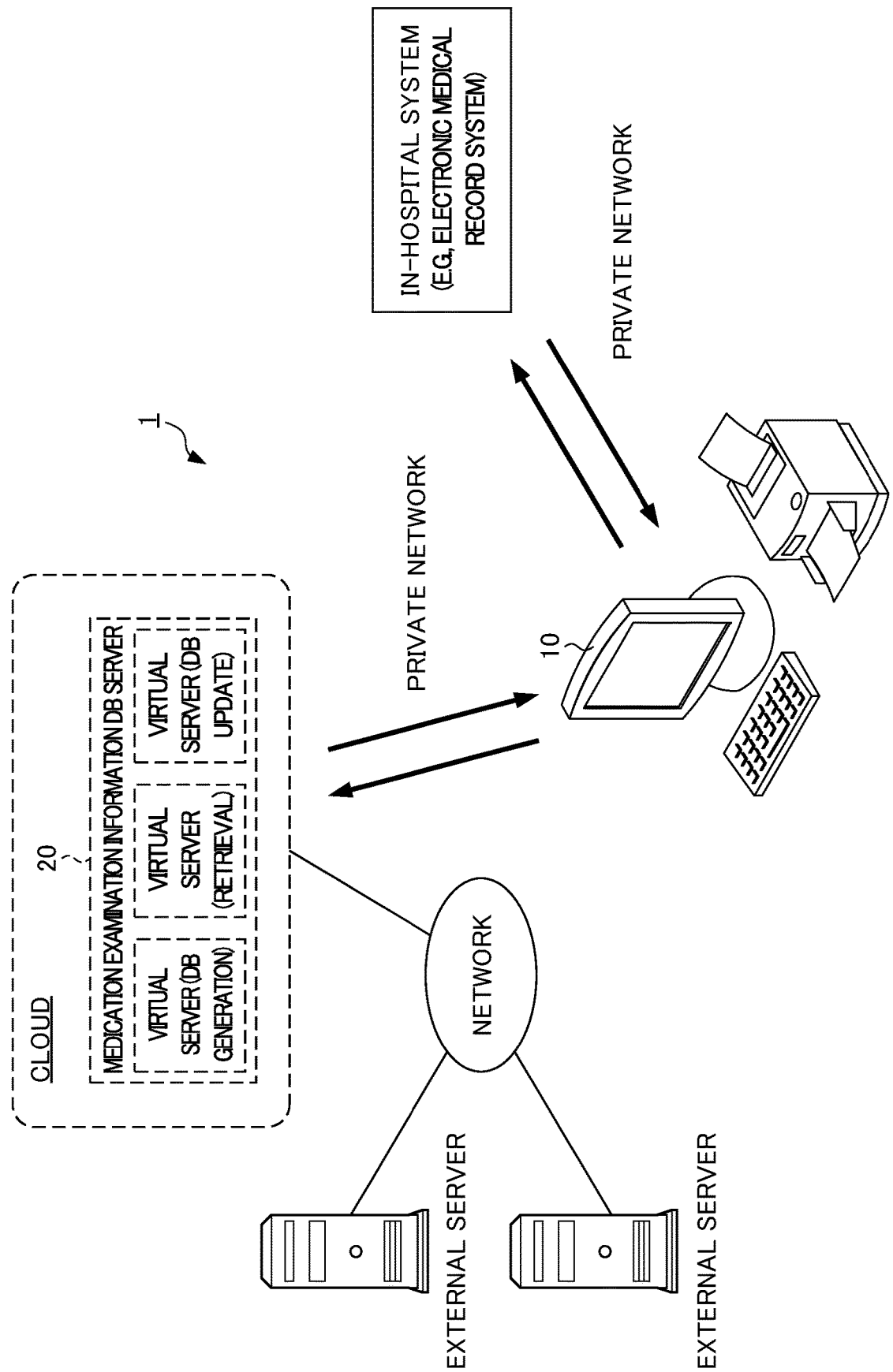
FIG. 8 is a diagram showing an example of a system configuration in which the medical information providing system 1 is implemented in the cloud at a higher level.

FIG. 8 is a diagram showing an example of a system configuration in which the medical information providing system 1 is implemented in the cloud at a higher level.

As shown in FIG. 8, the medication examination information DB server 20 is configured as a virtual server implemented in the cloud, and an API (Application Program Interface) for accepting a retrieval request as to whether or not a medication is a medication requiring clinical examination when prescribed, can be provided.

In this case, it is possible to easily use the functions of the medication examination information DB server 20 from various terminal devices 10 having different platforms, and the medical information providing system 1 is easy to use for many users.

Further, if the medication examination information DB server 20 is a virtual server implemented in the cloud, the functions of the medication examination information DB server 20 can be divided, and a virtual server can be configured for each function.

For example, as shown in FIG. 8, in the functions of the medication examination information DB server 20, a function of automatically generating the medication examination information DB 22b, a function of retrieving the medication examination information DB 22b, and a function of maintaining the medication examination information DB 22b (update of the medication examination information DB 22b, etc.), can be configured by different virtual servers.

As a result, since a plurality of functions provided in the medication examination information DB server 20 can be substantially separated, only the function to be used is operated, while the functions not used are suspended, so the medication examination information DB server 20 can be used flexibly.

Further, if the medication examination information DB server 20 is a virtual server implemented in the cloud, all of the medication examination information DB server 20 or part of the functions of the medication examination information DB server 20 may be duplicated by a plurality of virtual servers.

For example, in the functions of the medication examination information DB server 20, in response to an increase in the number of retrieval requests from the terminal device 10, or in order to provide operational convenience of the medication examination information DB server 20 (maintenance, etc.), the function to retrieve the medication examination information DB 22b, or the like, can be duplicated by a plurality of virtual servers.

In this way, it is possible to appropriately change the functional configuration according to the processing capability required for the medication examination information DB server 20 and operational convenience.

When changing the processing capability required for the medication examination information DB server 20, in addition to duplicating all of the medication examination DB server 20 or part of the functions of the medication examination information DB server 20 by a plurality of virtual servers, it is also possible to change the specification of the virtual server.

[Modification 2]

In the embodiments described above and the Modification 1, wherein the cloud type medical information providing system 1 is configured, a retrieval request is sent from the terminal device 10 to the medication examination information DB server 20, and it is determined whether or not the medication is a medication requiring clinical examination when it is prescribed.

Conversely, by providing the medication examination information DB in the terminal device 10, the function of the medical information providing system 1 may be implemented by a single information processing device (that is, realized as a stand-alone type system).

In this case, the medication document information acquiring unit 21a, the item-based condition setting unit 21b, the exception information acquiring unit 21c, the medication examination information extracting unit 21d, the medication document data storage unit 22a, the medication examination information DB 22b and the exception information storage unit 22c may be provided in the terminal device 10.

Figure 9:
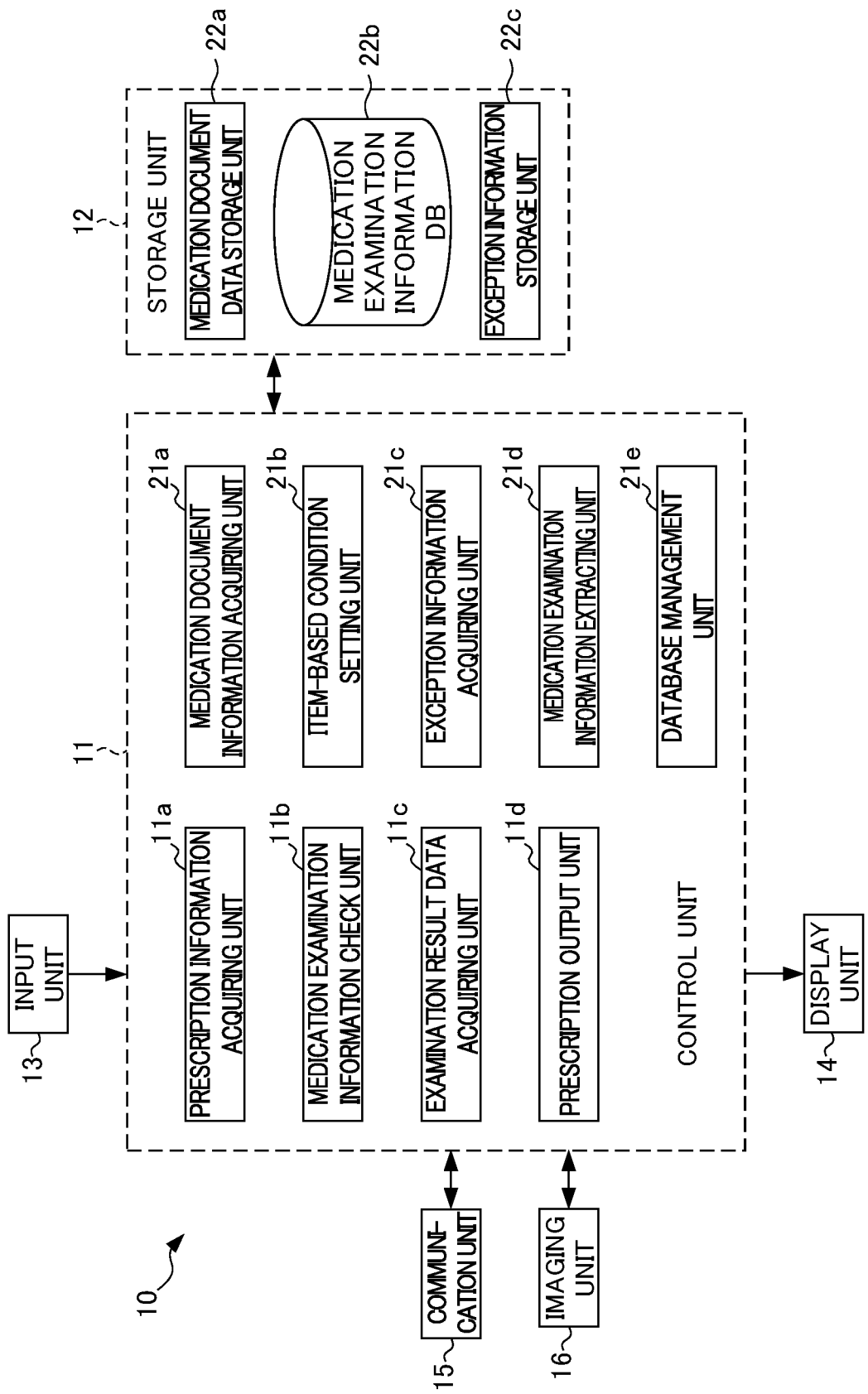
FIG. 9 is a schematic diagram showing a configuration in the case where the medical information providing system 1 is implemented by a single information processing apparatus.

FIG. 9 is a schematic diagram showing a configuration in the case where the medical information providing system 1 is implemented by a single information processing apparatus.

In FIG. 9, by providing the main functional configuration of the medication examination information DB server 20 shown in FIG. 2 in the terminal device 10, the function of the medical information providing system 1 is implemented by the terminal device 10 alone.

In the case of the configuration shown in FIG. 9, since a single apparatus can retrieve for medications that require clinical examination when they are prescribed, a doctor or a pharmacist can determine whether or not a medication that requires clinical examination is included in a prescription, and if it is included, the laboratory data items and the reference ranges of laboratory data can easily be confirmed, without using any network.

As described above, the medical information providing system 1 according to the present embodiment has, in the medication examination information DB server 20, a medication examination information extracting unit 21*d* (medication examination information extracting means, database generating means), and a database management unit 21*e* (medication examination information providing means).

The medication examination information extracting unit 21*d* extracts information on clinical examination relating to a medication that requires clinical examination when prescribed from at least one of package insert data and document data showing prescription guidelines concerning deterioration of organ function, for a plurality of types of medications.

In addition, the medication examination information extracting unit 21*d* generates a medication examination information database in which clinical examination information for the medication extracted by the medication examination information extracting means, is stored in association with the medication.

In response to a request from the terminal device 10, the database management unit 21*e* refers to the generated medication examination information database, and provides the information on clinical examination relating to the relevant medication for terminal device 10.

With such a configuration, it is possible to extract medications requiring clinical examination when they are prescribed, from the package insert data and the document data of guidelines, and to automatically generate the medication examination information DB including the laboratory data items and reference ranges of laboratory data and so on. Using the medication examination information DB generated in this manner, it is possible to more easily confirm whether the prescribed medication requires clinical examination for the patient or not.

The medical information providing system 1 further includes an item-based condition setting unit 21*b* in the medication examination information DB server 20.

The item-based condition setting unit 21*b* sets extraction conditions, for each item of the package insert data and the document data showing the guidelines, to extract the information on clinical examination relating to a medication requiring clinical examination when it is prescribed, in the package insert data and the document data showing the guidelines.

Further, in accordance with the extraction conditions set by the item-based condition setting unit 21*b*, the medication examination unit 21*d* extracts the information on clinical examination relating to a medication requiring clinical examination when it is prescribed, for each item of the package insert data and the document data showing the guidelines.

With such a configuration, by setting extraction conditions for each item of the package insert data and the document data, it is possible to set more appropriate extraction conditions reflecting the descriptive features of each item.

In the extraction conditions, a character string set for each item of the package insert data and the document data showing the guidelines, a specific character string correlated with the set character string, and a relationship between these character strings are defined.

With such a configuration, it is possible to automatically and appropriately extract laboratory data items or reference values or ranges of laboratory data included in the package insert data and the document data.

In addition, the medical information providing system 1 includes an exception information acquiring unit 21*c* (safety information acquiring means).

The exception information acquiring unit 21*c* acquires information on the safety of a medication which is not included in the medication examination information database.

The medication examination information extracting unit 21*d* refers to the medication examination information database and the information on the safety of a medication and provides the information on clinical examination relating to the relevant medication.

With such a configuration, it is possible to retrieve laboratory data items and reference values or ranges of laboratory data for medications requiring clinical examination when it is prescribed, including any safety information issued, before updating the medication examination information DB.

The medical information providing system 1 further includes the medication document information acquiring unit 21*a* (medication document information acquiring means).

The medication document information acquiring unit 21*a* acquires, for the plurality of types of medications, at least one of the package insert data, and the document data showing prescription guidelines concerning deterioration of organ function, from a preset acquisition target.

In addition, the medication document information acquiring unit 21*a* acquires and updates, for the plurality of medications, at least one of the package insert data and the document data showing prescription guidelines concerning deterioration of organ function at a preset timing.

With such a configuration, the contents of the medication examination information DB are updated to the latest state, and a more appropriate prescription can be issued.

The prescription P according to the present embodiment includes a patient information area P1, a medical institution information area P2, a standardized laboratory data area P3, and a drug-specific laboratory data area P4.

The patient information area P1 shows information about the patient.

The medical institution information area P2 shows the medical institution that issued the prescription.

The standardized laboratory data area P3 shows standardized laboratory data which are values of laboratory data common to a plurality of patients irrespective of the prescribed medication.

The drug-specific laboratory data area P4 shows values of laboratory data related to a medication requiring clinical examination when it is prescribed among medications prescribed to the patient, by identifying past change in the patient concerned.

With such a configuration, the state of the patient can be judged more accurately, and a medication can be prescribed more appropriately.

It should be noted that the above embodiment is not to limit the present invention. The present invention includes modifications, changes, etc. within a range in which the purpose of the present invention can be achieved.

For example, in the above embodiment, the prescription output by the medical information providing system 1 is described as being an outside hospital prescription, but the present invention is not limited thereto. That is, in addition to the medical information providing system 1 outputting an in-hospital prescription, it can be applied to various medical information providing media other than a prescription that prescribes medications.

In the above embodiment, the reference range of laboratory data related to the medication requiring clinical examination when prescribed, was described as being stored in the medication examination information DB, but the present invention is not limited thereto.

For example, the reference ranges related to a medication which requires clinical examination when prescribed, may be stored in the in-hospital system, and when the test result data acquiring unit 11c acquires the values of laboratory data, it may acquire the reference ranges of laboratory data together.

In the above embodiment, the description has assumed that the prescription P shows the change of value of laboratory data from left to right in the order of values of laboratory data for two times before, previous time, and current time (latest time), but the invention is not limited thereto.

In other words, in the medical examination value area P4, it suffices if the change of the patient's values of laboratory data is shown in such a way that they can be distinguished, for example, an increasing trend of past values of laboratory data may be represented by an upward-pointing arrow, a decreasing trend by a downward-pointing arrow, a maintenance trend by a rightward-pointing arrow, and the like. The change of past values of laboratory data may also be shown as a broken line, or the relative relationship of past values of laboratory data to a reference range of laboratory data may be shown in the display position by a predetermined symbol (dot, asterisk, etc.).

In the above embodiment, exception information on medication prescription was acquired from an independent administrative corporation, the Independent Administrative Institution of Pharmaceuticals and Medical Devices Agency, as an example, but the invention is not limited thereto. In other words, it is possible to acquire exception information issued by domestic or foreign public organizations similar to the Independent Administrative Institution of Pharmaceuticals and Medical Devices Agency.

In the above embodiment, when outputting the outside hospital prescription as electronic data, in addition to using the unique data format of the medical information providing system 1, prescription data in a specific, public format may also be used. For example, an electronic prescription devised by the Ministry of Health, Labor and Welfare may be available to the medical information providing system 1, and outside hospital prescription data comprehensively including this electronic prescription may be issued. By making the outside hospital prescription data corresponding to the specific format that is being used publicly, it is possible to more easily cooperate with electronic medicine notebooks and medical information managed by medical institutions.

In the above embodiment, when configuring the medical information providing system 1 as a cloud system, the medication examination information DB server 20 may make different responses according to the system (the medical-related system to which the terminal device 10 belongs) that made API requests to the medication examination information DB server 20, or the level (types of authorities) of the user (doctor, etc.). For example, even if the request is made by the same API, the medication examination information DB server 20 may transmit the retrieved result of contents corresponding to the requesting system or level of the user.

When assigning a level (authority) to the requesting system or user, the level can be set in units of organizations such as medical institutions, medical facilities, departments or the like, and units of medical personnel such as doctors and pharmacists. In addition, on the user side of the medical information providing system 1, the administrator who manages the system may be given the authority of an administrator (full access permission, for example).

By doing so, it is possible to provide an appropriate retrieved result considering the authority of the user while enabling the use of a shared interface by the API.

EXPLANATION OF REFERENCE NUMERALS 1 medical information providing system, 10 terminal device, 11, 21 control unit, 11a prescription information acquiring unit, 11b medication examination information check unit, 11c examination result data acquiring unit, 11d prescription output unit, 21a medication document information acquiring unit, 21b item-based condition setting unit, 21c exception information acquiring unit, 21d medication examination information extracting unit, 21e database management unit, 12, 22 storage unit, 22a medication document data storage unit, 22b medication examination information DB, 22c exception information storage unit, 13, 23 input unit, 14, 24 display unit, 15, 25 communication unit, 16 imaging unit, 20 medication examination information DB server, P prescription, P1 patient information area, P2 medical institution information area, P3 standardized laboratory data area, P4 drug-specific laboratory data area.

The invention claimed is:

1. A medical information providing system including a prescription issuing device and a server which are configured to be able to communicate with each other,
wherein the prescription issuing device is a device for issuing a prescription for a patient and comprises a first processor, wherein the first processor executes: acquiring prescription data on the patient, and
wherein the server comprises a second processor, wherein the second processor executes:
extracting, for each of a plurality of types of medications requiring clinical examination for the patient when it is prescribed, information on clinical examination relating to the medication by extracting character strings from one or both of package insert data for the medication and document data showing prescription guidelines concerning deterioration of organ function for the medication, wherein the character strings are extracted based on extraction conditions;
generating a medication examination information database by associating in storage, for each of the plurality of types of medications, the clinical examination information for the medication extracted by the medication examination information extracting processing and an identifier for the medication; and
retrieving from the medication examination information database generated, the information on clinical examination relating to a medication in response to requests received from the prescription issuing device, and transmitting the information on clinical examination relating to the medication as retrieved, to the prescription issuing device, wherein
the information on clinical examination relating to the medication includes information on whether clinical examination for the patient is required when the medication is prescribed, and a reference range of laboratory data of the patient in a case in which clinical examination is required, the first processor further executes: acquiring laboratory data of the patient, the laboratory data corresponding to the information on clinical examination relating to the medication, and automatically adding, to the prescription data, a data item of the laboratory data of the patient, the data item not being included in the prescription data, and thereby issues the prescription.

2. The medical information providing system according to claim 1, wherein the second processor further executes:

setting the extraction conditions for the character strings, for each item of the package insert data and the document data showing the guidelines, to extract the information on clinical examination for a patient relating to a medication requiring clinical examination when it is prescribed, in the package insert data and the document data showing the guidelines; and extracting the information on clinical examination relating to a medication requiring clinical examination for a patient when it is prescribed, for each item of the package insert data and the document data showing the guidelines, according to the extraction conditions set by the condition setting processing.

3. The medical information providing system according to claim 2, wherein, in the extraction conditions set, a character string set for each item of the package insert data and the document data showing the guidelines, a specific character string correlated with the set character string, and a relationship between these character strings are defined.

4. The medical information providing system according to claim 1, wherein the second processor further executes:

acquiring information on the safety of a medication which is not included in the medication examination information database generated and stores the information in a storage unit;

retrieving the medication examination information database generated, and the information on the safety of a medication acquired; and providing the information on clinical examination relating to the medication.

5. A medical information providing system according to claim 4, wherein the second processor further executes:

acquiring, for the plurality of types of medications, one or both of the package insert data, and the document data showing prescription guidelines concerning deterioration of organ function, from a preset external database; and acquiring and updating, for the plurality of medications, one or both of the package insert data and the document data showing prescription guidelines concerning deterioration of organ function at a preset timing, from the external database.

6. A server in a medical information providing system including a prescription issuing device and a server which can communicate with each other, wherein the prescription issuing device is a device for issuing a prescription for a patient and comprises a first processor, wherein the first processor executes: acquiring prescription data on the patient; and acquiring laboratory data of the patient, based on information on clinical examination relating to a medication, the information on clinical examination being transmitted from the server, and the prescription issuing device automatically adds, to the prescription data, a data item of the laboratory data of the patient, the data item not being included in the prescription data, and thereby issues the prescription, the server comprising a second processor, wherein the second processor executes:

extracting, for each of a plurality of types of medications requiring clinical examination for the patient when it is prescribed, information on clinical examination relating to the medication by extracting character strings from one or both of package insert data for the medication and document data showing prescription guidelines concerning deterioration of organ function for the medication, wherein the character strings are extracted based on extraction conditions;

generating a medication examination information database by associating in storage, for each of the plurality of types of medications, the clinical examination information for the medication extracted by the medication examination information extracting processing and an identifier for the medication; and retrieving from the medication examination information database generated by the database generating processing, the information on clinical examination relating to a medication in response to requests received from the prescription issuing device, and transmits the information on clinical examination relating to the medication as retrieved, to the prescription issuing device, wherein the information on clinical examination relating to the medication includes information on whether clinical examination for the patient is required when the medication is prescribed, and a reference range of laboratory data of the patient in a case in which clinical examination is required.

7. A medical information providing apparatus for providing information to be added to prescription data on a patient, the medical information providing apparatus comprising a processor, wherein the processor executes:

extracting, for each of a plurality of types of medications requiring clinical examination for the patient when it is prescribed, information on clinical examination relating to the medication by extracting character strings from one or both of package insert data for the medication and document data showing prescription guidelines concerning deterioration of organ function for the medication, wherein the character strings are extracted based on extraction conditions;

generating a medication examination information database by associating in storage, for each of the plurality of types of medications, the clinical examination information for the medication extracted by the medication examination information extracting processing and an identifier for the medication;

retrieving the information on clinical examination relating to the medication associated with the medication from the medication examination information database generated by the database generating processing, and transmitting the information on clinical examination relating to the medication as retrieved; and acquiring prescription data on the patient; and acquiring laboratory data of the patient, wherein the information on clinical examination relating to the medication includes information on whether clinical examination for the patient is required when the medication is prescribed, and a reference range of laboratory data of the patient in a case in which clinical examination is required, the processor acquires the laboratory data of the patient, the laboratory data corresponding to the information on clinical examination relating to the medication, and the processor provides a data item of the laboratory data of the patient as the information to be added to the prescription data on the patient, the data item not being included in the prescription data.

8. A medical information providing apparatus for issuing a prescription, the medical information providing apparatus comprising a processor, wherein the processor executes:

acquiring prescription data on a patient;

confirming whether or not a medication requiring clinical examination for the patient is included in prescription data by retrieving a medication examination information database storing information on clinical examination relating to a medication requiring clinical examination for a patient when it is prescribed;

acquiring laboratory data of a laboratory data item related to a medication when data on the prescription includes a medication requiring clinical examination for a patient when it is prescribed; and issuing a prescription in which the prescription data is acquired and the laboratory data is acquired, wherein the information on clinical examination relating to the medication includes information on whether clinical examination for the patient is required when the medication is prescribed, and a reference range of laboratory data of the patient in a case in which clinical examination is required, the processor further executes:

issuing a prescription by identifying whether the laboratory data acquired is included in the reference range of the laboratory data of the patient, and automatically adding, to the acquired prescription data, a data item of the laboratory data of the patient, the data item not being included in the acquired prescription data, and thereby issues the prescription.

9. A medical information providing medium issued based on prescription data on a patient, the medical information providing medium comprising:

a patient information area for showing information about the patient, the information being included in the prescription data;

a medical institution information area for showing a medical institution that issued a prescription, the medical institution being included in the prescription data;

a standardized laboratory data area for showing standardized laboratory data common to a plurality of patients irrespective of a prescribed medication, the standardized laboratory data being retrieved based on the prescription data and automatically added by an apparatus that issues the medical information providing medium; and a drug-specific laboratory data area for showing values of laboratory data related to a medication requiring clinical examination for the patient when it is prescribed among medications prescribed, the drug-specific laboratory data being retrieved based on the prescription data and automatically added by an apparatus that issues the medical information providing medium, to the patient, by identifying past change in the patient concerned, wherein the standardized laboratory data and the drug-specific laboratory data are shown by identifying whether the data is included in the reference range of the laboratory data of the patient.

10. A medical information providing method for issuing a prescription, the medical information providing method comprising:

acquiring prescription data on a patient;

extracting, for each of a plurality of types of medications requiring clinical examination for the patient when it is prescribed, information on clinical examination relating to the medication by extracting character strings from one or both of package insert data for the medication and guideline data showing prescription guidelines concerning deterioration of organ function for the medication, wherein the character strings are extracted based on extraction conditions;

generating a medication examination information database by associating in storage, for each of the plurality of type of medications, the clinical examination information for the medication extracted and an identifier for the medication;

retrieving from the medication examination information database generated, the information on clinical examination relating to a medication to transmit the information on clinical examination relating to the medication as retrieved, wherein the information on clinical examination relating to the medication includes information on whether clinical examination for the patient is required when the medication is prescribed, and a reference range of laboratory data of the patient in a case in which clinical examination is required;

acquiring laboratory data of the patient, the laboratory data corresponding to the information on clinical examination relating to the medication; and automatically adding, to the prescription data, a data item of the laboratory data of the patient, the data item not being included in the prescription data, and issuing the prescription.

11. A medical information providing method for issuing a prescription, the medical information providing method comprising:

acquiring prescription data on a patient; confirming whether or not a medication requiring clinical examination for the patient is included in prescription data by retrieving a medication examination information database storing information on clinical examination relating to a medication requiring clinical examination for a patient when it is prescribed;

acquiring laboratory data of a laboratory data item related to a medication when data on the prescription includes a medication requiring clinical examination for a patient when it is prescribed; and issuing a prescription in which the prescription data is acquired and the laboratory data is acquired, wherein the information on clinical examination relating to the medication includes information on whether clinical examination for the patient is required when the medication is prescribed, and a reference range of laboratory data of the patient in a case in which clinical examination is required, the issuing a prescription issues a prescription by identify whether the laboratory data acquired is included in the reference range of the laboratory data of the patient, and the medical information providing method further includes automatically adding, to the acquired prescription data, a data item of the laboratory data of the patient, the data item not being included in the acquired prescription data, and issuing the prescription.

12. A non-transitory storage medium encoded with a computer-readable program that controls a processor to execute:
- acquiring prescription data on a patient;
- extracting, for each of a plurality of types of medications requiring clinical examination for the patient when it is prescribed, information on clinical examination relating to the medication by extracting character strings from one or both of package insert data for the medication and guideline data showing prescription guidelines concerning deterioration of organ function for the medication, wherein the character strings are extracted based on extraction conditions;
- generating a medication examination information database by associating in storage, for each of the plurality of type of medications, the clinical examination information for the medication extracted and an identifier for the medication;
- retrieving from the medication examination information database generated, the information on clinical examination relating to a medication to transmit the information on clinical examination relating to the medication as retrieved, wherein the information on clinical examination relating to the medication includes information on whether clinical examination for the patient is required when the medication is prescribed, and a reference range of laboratory data of the patient in a case in which clinical examination is required;
- acquiring laboratory data of the patient, the laboratory data corresponding to the information on clinical examination relating to the medication; and
- automatically adding, to the prescription data, a data item of the laboratory data of the patient, the data item not being included in the prescription data, and issuing the prescription.

13. A non-transitory storage medium encoded with a computer-readable program that controls a processor to execute:
- acquiring prescription data on a patient;
- confirming whether or not a medication requiring clinical examination for the patient is included in prescription data by retrieving a medication examination information database storing information on clinical examination relating to a medication requiring clinical examination for a patient when it is prescribed;
- acquiring laboratory data of a laboratory data item related to a medication when data on the prescription includes a medication requiring clinical examination for a patient when it is prescribed; and
- issuing a prescription in which the prescription data is acquired by the acquiring prescription data and the laboratory data is acquired by the acquiring laboratory data, wherein
- the information on clinical examination relating to the medication includes information on whether clinical examination for the patient is required when the medication is prescribed, and a reference range of laboratory data of the patient in a case in which clinical examination is required,
- the issuing a prescription issues a prescription by identify whether the laboratory data acquired is included in the reference range of the laboratory data of the patient, and
- the computer-readable program further controls the processor to execute:
  - automatically adding, to the acquired prescription data, a data item of the laboratory data of the patient, the data item not being included in the acquired prescription data, and issuing the prescription.

14. The medical information providing system according to claim 2, wherein the second processor further executes:
- acquiring information on the safety of a medication which is not included in the medication examination information database generated and stores the information in a storage unit;
- retrieving the medication examination information database generated by the database generating processing, and the information on the safety of a medication acquired; and
- providing the information on clinical examination relating to the medication.

15. The medical information providing system according to claim 3, wherein the second processor further executes:
- acquiring information on the safety of a medication which is not included in the medication examination information database generated and stores the information in a storage unit;
- retrieving the medication examination information database generated, and the information on the safety of a medication acquired; and
- providing the information on clinical examination relating to the medication.

* * * * *